United States Patent [19]  [11] Patent Number: 5,017,479
Eyssautier  [45] Date of Patent: May 21, 1991

[54] PROCESS FOR MULTIPLICATION OF POLYSACCHARIDE-PRODUCING MICROORGANISMS AND USE THEREOF IN A POLYSACCHARIDE PRODUCTION PROCESS

[75] Inventor: Bruno Eyssautier, Carentan, France
[73] Assignee: Sanofi, Paris, France
[21] Appl. No.: 311,775
[22] Filed: Feb. 17, 1989
[30] Foreign Application Priority Data
Feb. 18, 1988 [FR] France ............................. 88 01933
[51] Int. Cl.$^5$ .................. C12P 19/04; C12R 1/00; C12R 1/645; C12N 1/22
[52] U.S. Cl. ............................ 435/101; 435/42; 435/102; 435/103; 435/104; 435/200; 435/201; 435/244; 435/245; 435/252; 435/252.1; 435/253.6; 435/254; 435/822; 435/829; 435/831; 435/874; 435/910; 435/911
[58] Field of Search .............. 435/42, 101, 102, 103, 435/104, 200, 201, 244, 245, 252, 252.1, 253.6, 254, 822, 829, 831, 874, 910, 911

[56] References Cited
U.S. PATENT DOCUMENTS

| | | | |
|---|---|---|---|
| 4,075,405 | 2/1978 | Takahashi et al. | 435/101 |
| 4,311,796 | 1/1982 | Weisrock | 435/104 |
| 4,338,399 | 7/1982 | Weil et al. | 435/105 |
| 4,355,106 | 10/1982 | Lawford . | |
| 4,374,929 | 2/1983 | Weisrock | 435/104 |
| 4,416,990 | 11/1983 | Rinaudo et al. | 435/104 |
| 4,431,734 | 2/1984 | Rinaudo et al. | 435/42 |
| 4,692,408 | 9/1987 | Banks et al. | 435/101 |
| 4,775,632 | 10/1988 | Gozard et al. | 435/104 |

FOREIGN PATENT DOCUMENTS
2090847  7/1982  United Kingdom .

OTHER PUBLICATIONS

Patent Abstracts of Japan, vol. 9, No. 188 (C-295) (1911), "Production of Xanthan Gum", Aug. 3, 1985.
Journal of Applied Bacteriology, 1982, 53,385–393, "An Enzyme System Hydrolysing the Polysaccharides of Xanthomonas Species", by J. W. Sutherland.
Development in Industrial Microbiology, vol. 21, Proceedings of the 36th General Meeting of the Society for Industrial Microbiology, Pittsburg, Pa., Aug. 11–17, 1979, Chapter 49, pp. 451–460, W. L. Griffith et al., "Modification of Biopolymer Solution Properties . . . ".

Primary Examiner—Herbert J. Lilling
Attorney, Agent, or Firm—Foley & Lardner

[57] ABSTRACT

Process for obtaining a mass of polysaccharide-producing microorganisms, consisting in conducting the growth of the microorganisms in a medium containing an enzyme which hydrolyzes the formed polysaccharide.

Application in a process for the production of polysaccharide in two stages, in which the growth stage takes place in the presence of an enzyme, particularly for the production of scleroglucane using sclerotium type fungi.

10 Claims, No Drawings

PROCESS FOR MULTIPLICATION OF POLYSACCHARIDE-PRODUCING MICROORGANISMS AND USE THEREOF IN A POLYSACCHARIDE PRODUCTION PROCESS

The present invention relates to a process for producing polysaccharides by fermentation, in two stages, such that, during the first stage of production of the biomass, there is virtually no polysaccharide present in the culture medium.

Most microorganisms producing polysaccharides, i.e., bacteria or fungi, secrete the polymer during their growth, and the pre-culture media become rapidly viscous; this reduces the efficiency of the stirring and aeration of the medium and limits as a result the rate of production of the biomass and the maximum cellular concentration which can be reached. Various solutions have been proposed to dissociate the cellular growth from the polysaccharide production. One of these solutions consists in using, in a continuous process for the production of xanthan, a medium depleted in carbohydrates, such as described in U.S. Pat. No(s). 3,328,282 and 3,251,749 or as described in EP-A-0,112,661. A second solution consists in introducing in the preculture medium as sole carbon-containing nutrient, a compound which will not allow the biosynthesis of the polysaccharide such as xylose or glycerol for the xanthan-producing *Xanthomonas campestris.*

However, with the first solution, it is difficult to control the carbohydrate concentration to have only a weak biosynthesis of polysaccharides while maintaining a satisfactory growth, whereas with the second solution, it has been found that carbon-containing nutrients blocking polysaccharide secretion during growth are only known for a few types of microorganisms and that, in particular, they do not seem to be effective for all the species of that microorganism.

It is not the object of the present invention to inhibit the secretion of the polysaccharide during the preculture stage, but instead to decompose it, by the enzymatic route, as its formation progresses.

A first object of the invention is a process for the production of a mass of microorganisms producing thickening polysaccharides, which process consists in cultivating these microorganisms in a medium promoting their growth and containing an enzyme which catalyzes the decomposition of the resulting polysaccharide.

Said process can be used for obtaining a biomass of bacteria or fungi producing a thickening polysaccharide such as the xanthane-producing Xanthomonas type bacteria, and in particular the *Xanthomonas begioniae, Xanthomonas campestris, Xanthomonas vesicatoria* and *Xanthomonas pisi* species, the alginic acid-producing bacteria of Azobacter type and in particular bacteria of the *Azobacter vinelandii* species and bacteria of the *Agrobacterium radiobacter* and *Alcaligenes faecalis* species and the succinoglucane-producing *Pseudomonas myxogenes,* the dextrane-producing bacteria of the *Leuconostoc mesenteroides* species, and the scleroglucane-producing fungi of the Sclerotium type, such as described in U.S. Pat. No. 3,301,848.

The enzymes used are selected as a function of the produced polysaccharide.

For example, to obtain Xanthomonas it is possible to use the enzymatic composition produced by a Bacillus train, either pure or mixed with a Flavobacterium strain, as described in Dev. Ind. Microbiol., 26, pages 281-288 (1984) or the composition described in J. Ind. Microbiol. pages 31-37 (1986).

For producing Sclerotium, there is for example the beta-1,3-glucanase of Basidiomycetes mentioned by F. E. Halleck in U.S. Pat. No. 3,423,288 or that obtained by culture of *Sporotrichum dimorphosporum,* and in particular by culture of the strain deposited at the ATCC under No. 24562 and the beta-1,3 beta-1,6 glucanase, marketed by Novo (Denmark) under the trademark Glucanex ® or that marketed by Gist-Brocades under the trademark Rapidase GL 150.

For obtaining *Leuconostoc mesenteroides,* there is for example the *Streptococcus mutans* dextranase described in "Molecular Microbiology and Immunology of Streptococcus mutans", S. Humada et al. - Elsevier Sc. Pub. (1986), pages 205-215, or fungic dextranase issued from *Penicillium lilacinum* marketed by Novo as well as the beta-1,3 beta-1,6 glucanases.

The amounts of enzyme to be introduced into the preculture medium are dependent on the nature and purity of the enzyme, of the polysaccharide and of its rate of production in growth stage; preliminary tests will enable one skilled in the art to determine the efficient concentration for each case.

Similarly, the enzymes selected among the available enzymes for degrading the considered polysaccharide, will be those which exhibit a good enzymatic activity at the pH and temperature conditions of preculture, and which can be inactivated before or during production stage.

Another object of the invention is the process for the production of a polysaccharide by fermentation, in two stages, which consists in preparing a certain quantity of secreting microorganisms by preculture in the presence of an enzyme hydrolyzing the polysaccharide, and in cultivating the microorganisms to produce the polysaccharide in a medium adapted for such production. Such a process has the particular advantage of giving substantially the same quantity of polysaccharide as a conventional process, but in clearly shorter times.

The conditions of preculture and fermentation may be selected either to induce hydrolysis during growth or on the contrary to inhibit same during the production stage; the choice of, for example, the pH of the preculture and culture media and/or of the temperature may be one way of stimulating or inactivating the enzyme; in certain cases, conventional media may be used. A repressor of the enzyme or an allosteric effector may also be introduced into the medium, at the end of the preculture.

Eventually, in order to neutralize the enzymatic activity, the broth may be submitted at the end of preculture to a temperature, or a pH, which will denature the selected enzyme.

During the preculture stage the product used as carbon-containing nutrient for the microorganism may be introduced in the culture medium in considerably smaller quantity, if carbohydrates assimilable by the microorganisms are released in the medium by the hydrolysis of the polysaccharide. For example, in a preculture of *Sclerotium rolfsii,* the contents of exogenous glucose will be reduced by at least 70%.

A small enzymatic activity remaining in the medium during the production stage, is acceptable provided that the hydrolysis of the polysaccharide releases carbohydrates which can be used as a carbon-containing nutrient by the microorganisms.

The following describes, by way of example, the application of the process, according to the invention, for the production of scleroglucane by fermentation of the *Sclerotium rolfsii* fungus.

EXAMPLE

Preculture: production of *Sclerotium rolfsii* from frozen sclerotium of the ATCC strain No. 15206.

(a) Revitalization of the fungus:

5 frozen sclerotia are introduced in an Erlenmeyer flask containing 100 ml of an aqueous sterilized medium comprising 4.5 g of glucose, 0.2 g of $NaNO_3$, 0.1 g of yeast extract, 0.1 g of $KH_2PO_4$, 0.025 g of $MgSO_4$ and 0.0005 g of thiamine.

The closed flask is left to incubate, under stirring, at 28° C. for 96 hours.

(b) Preparation of a first inoculum in a 6-liter fermenter, under stirring:

The contents of 4 revitalizing flasks are introduced in 4 liters of an aqueous sterilized medium comprising 176 g of glucose, 8 g of $NaNO_3$, 40 g of yeast extract, 4 g of $KH_2PO_4$, 4 g of $MgSO_4$, 0.02 g of thiamine and 4 g of antifoam such as Pluronic ® and 160 mg of sterile Glucanex ® are added.

The medium is kept for 44 hours at 28° C. under stirring, the pH being kept at 4.5 by addition of a 10 aqueous solution of sodium hydroxide.

(c) Preparation of a second inoculum in a 15-liter fermenter under stirring:

1 liter of the inoculum obtained hereinabove is introduced in 10 liters of an aqueous sterilized medium comprising 350 g of glucose, 28 g of $NaNO_3$, 7.2 g of corn soaking liquor, 7 g of $KH_2PO_4$, 10.5 g of $MgSO_4$, 0.05 g of thiamine and 5 g of Pluronic ® and 400 mg of Glucanex ®.

The whole mixture is kept for 24 hours at 28° C. under stirring.

The medium thus obtained contains an important quantity of biomass, representing, at the end of incubation time, 10 g for every kilo of medium instead of 2 g/kg in a conventional fermentation.

(c) Production of scleroglucane:

10 l of an aqueous sterilized medium comprising 350 g of glucose, 14 g of $NaNO_3$, 3.6 g of corn soaking liquor, 10.5 g of $MgSO_4$, 7 g of $KH_2PO_4$, 5 g of Pluronic ® and one liter of inoculum are introduced in a 15-liter fermenter of the same type as that used for preparing the inoculum.

The whole mixture is left to incubate for 38 and a half hours at 28° C. under stirring, the pH being kept at 3 by adding a 10% aqueous solution of NaOH.

The fermentation medium is thereafter treated in a conventional manner depending on the target application, either the biomass is separated by filtration and the scleroglucane is precipitated by adding an alcoholic solvent such as isopropanol, or an alcoholic solvent is added to the fermentation medium and the formed precipitate is isolated.

The same quantity of scleroglucane is obtained with the process according to the invention as in a conventional fermentation without enzyme, the quantity of formed polysaccharide being essentially dependent on the quantity of glucose present in the medium; on the other hand, the fermentation time in a conventional process, without the enzyme, would be 48 hours instead of 36 and a half hours.

What is claimed is:

1. A process for obtaining a mass of polysaccharide-producing microorganisms, comprising the step of growing an inoculum of polysaccharide-producing microorganisms in a growth medium to produce a mass of said microorganisms, wherein said microorganisms produce polysaccharide in the course of their growth, and wherein said growth is effected in a medium containing an enzyme which hydrolyzes said polysaccharide.

2. A process as claimed in claim 1, wherein the microorganism is a fungus of the genus Sclerotium, producing scleroglucane.

3. A two-stage process for producing a polysaccharide by fermentation, comprising the steps of:
    (a) obtaining a mass of polysaccharide-producing microorganisms by a process as claimed in claim 1, and
    (b) culturing said mass of polysaccharide-producing microorganisms in a nutrient medium to produce said polysaccharide, wherein said enzyme that hydrolyzes said polysaccharide in step (a) is substantially inactivated during step (b).

4. A process as claimed in claim 3, wherein the enzyme is inhibited at the end of the growth stage by modification of the pH or of the temperature.

5. A process as claimed in claim 4, wherein the enzyme is inactivated during the production stage by fixing the pH at a suitable value.

6. A process as claimed in any one of claims 3 to 5, wherein the microorganism is a scleroglucane-producing fungus of the genus Sclerotium.

7. A process as claimed in claim 6, wherein the enzyme is a beta-1,3 glucanase.

8. A process as claimed in claim 7, wherein the enzyme is a beta-1,3 beta-1,6 glucanase.

9. A process as claimed in claim 7, wherein the pH of the production medium is 3.

10. A process as claimed in claim 8, wherein the pH of the production medium is 3.

* * * * *